United States Patent

Remmler

[19]

[11] Patent Number: 5,993,448
[45] Date of Patent: Nov. 30, 1999

[54] IMPLANTABLE APPARATUS, MATRIX AND METHOD FOR CORRECTION OF CRANIOFACIAL BONE DEFORMITIES

[76] Inventor: Daniel J. Remmler, 2330 S. 17th St., Lincoln, Nebr. 68502

[21] Appl. No.: 09/051,011
[22] PCT Filed: Oct. 1, 1996
[86] PCT No.: PCT/US96/15716
   § 371 Date: Mar. 31, 1998
   § 102(e) Date: Mar. 31, 1998
[87] PCT Pub. No.: WO97/12568
   PCT Pub. Date: Apr. 10, 1997

Related U.S. Application Data

[60] Provisional application No. 60/004,658, Oct. 2, 1995.

[51] Int. Cl.⁶ ................................................... A61B 17/56
[52] U.S. Cl. ................................ 606/53; 606/57; 606/70
[58] Field of Search ........................... 606/53, 54, 57, 606/58, 70, 71, 105

[56] References Cited

U.S. PATENT DOCUMENTS

| | | | |
|---|---|---|---|
| 4,011,602 | 3/1977 | Rybicki et al. | 3/1.9 |
| 4,308,863 | 1/1982 | Fischer | 606/57 |
| 4,615,338 | 10/1986 | Ilizarov et al. | 128/92 |
| 4,978,348 | 12/1990 | Ilizarov | 606/57 |
| 5,108,394 | 4/1992 | Kurokawa et al. | 606/59 |
| 5,147,358 | 9/1992 | Remmler | 606/57 |
| 5,152,280 | 10/1992 | Danieli | 606/54 |
| 5,190,543 | 3/1993 | Schläpfer | 606/61 |
| 5,203,783 | 4/1993 | Härle | 606/53 |
| 5,364,396 | 11/1994 | Robinson et al. | 606/53 |
| 5,439,377 | 8/1995 | Milanovich | 433/7 |
| 5,454,810 | 10/1995 | Pohl et al. | 606/59 |
| 5,505,733 | 4/1996 | Justin et al. | 606/63 |
| 5,514,180 | 5/1996 | Heggeness et al. | 623/17 |
| 5,540,687 | 7/1996 | Fairley et al. | 606/60 |

OTHER PUBLICATIONS

Cohen et al., "Distraction Osteogenesis of the Human Craniofacial Skeleton: Initial Experience with a New Distraction System," *J. Craniofacial Surgery*, vol. 6. No. 5, pp. 368–374, Sep. 1995.

Rachmiel et al., "Multiple Segmental Gradual Distraction of Facial Skeleton: An Experimental Study," *Analysis of Plastic Surgery*, vol. 36, No. 1, pp. 52–59, Jan. 1996.

Cohen et al., "Maxillary–Midface Distraction in Children with Cleft Lip and Palate: A Preliminary Report," *Plastic and Reconstructive Surgery*, pp. 1421–1428, Apr. 1997.

International Seach Report, Application No. PCT/US96/15716, mailed Dec. 27, 1996.

*Primary Examiner*—Michael Buiz
*Assistant Examiner*—Julian W. Woo
*Attorney, Agent, or Firm*—Marshall, O'Toole, Gerstein, Murray & Borun

[57] ABSTRACT

An apparatus for relative movement of first and second bone segments, such as segments of a skull, includes first and second nodes attachable to first and second bone segments, respectively, and a first rod mechanism flexibly attached to both the first and second nodes. The rod mechanism is either extendible or retractable along an axis thereof. The rod mechanism axis is pivotable with respect to the first and second nodes in at least a first plane parallel to a plane tangent to the skull. The rod mechanism axis also is pivotable with respect to the first and second nodes in a second plane perpendicular to the first plane.

29 Claims, 6 Drawing Sheets

IMPLANTABLE APPARATUS, MATRIX AND METHOD FOR CORRECTION OF CRANIOFACIAL BONE DEFORMITIES

CROSS REFERENCE TO RELATED APPLICATIONS

This is a continuation-in-part of pending provisional U.S. application Ser. No. 60/004,658, filed Oct. 2, 1995.

BACKGROUND OF THE INVENTION

1. Field of the Invention

The invention relates to bone distractive and contractive movements and more particularly, to apparatus and methods for the correction of craniofacial bone deformities.

2. Description of Related Technology

Human children born with skull and facial (craniofacial) bone growth disorders known as craniosynostosis develop profound abnormalities in the shape and function of the craniofacial skeleton. The underlying causative factor is the congenital absence of anatomically normal sutures (lines of open bone) between the various segments of craniofacial bone. This fusion of the normal bone lines, or synostosis, leads to unbalanced bone growth and subsequent deformation. The traditional treatment for these disorders has been surgical exposure, and transfer of the bones to create a more normal architecture. Such surgery requires neurosurgical exposure of the brain and its surrounding tissues. Also, bone grafts, plating, wires, and other rigid fixation implants are required to stabilize the repositioned bones.

Alternative methods for correcting synostotic deformities in young infants without the risk of major intracranial surgery and bone grafts have been introduced. For example, Remmler, U.S. Pat. No. 5,147,358 discloses an apparatus which was utilized to gradually reposition the cranial and fronto-facial bones in a rabbit model by mechanical means to a degree proportionate to that required in humans with craniosynostosis. Stainless steel fixation plates with threaded tubes were attached with screws to the craniofacial bones. Next, threaded percutaneous (through the skin) pins were attached to the plates. The bones were then gradually repositioned over a period of approximately one and one-half months to the desired position using an external jack-screw mechanism.

The device disclosed in U.S. Pat. No. 5,147,358 has been used to successfully distract bone segments primarily in one dimension. However, congenital craniofacial anomalies are frequently asymmetric in three dimensions, requiring simultaneous distractive and contractive movements of multiple major bone segments. Thus, a need exists for a versatile, multi-axial apparatus, system, and method for moving multiple bone segments in various directions.

SUMMARY OF THE INVENTION

It is an object of the invention to overcome one or more of the problems described above. Further objects of the invention include providing subcutaneous craniotatic apparatus and matrix which offers the advantages of complete implantation under the skin and multi-axial distraction capability, and including a method for guiding bones during their transit, preferably with computer aided accuracy.

An apparatus of the invention for relative movement of first and second bone segments, such as portions of a skull, includes first and second nodes attachable to first and second bone segments, respectively, and a first rod mechanism flexibly attached to both the first and second nodes. The rod mechanism is either extendible or retractable along an axis thereof. The rod mechanism axis is pivotable with respect to the first and second nodes in at least a first plane parallel to a plane tangent to the skull. The rod mechanism axis also is pivotable with respect to the first and second nodes in a second plane perpendicular to the first plane.

Also according to the invention, a matrix for correcting craniofacial bone deformities includes a first node disposed on a first bone segment; a second node disposed on a second bone segment; and a first rod mechanism flexibly attached to both the first node and the second node. The first rod mechanism is extendible and/or retractable along an axis thereof. The matrix also includes a third node which is disposed on one of the first bone segment, the second bone segment, or a third bone segment neighboring the first bone segment. A second rod mechanism is attached to both the first node and the third node. The second rod mechanism is either extendible, retractable, extendible and retractable, or static along an axis thereof.

Furthermore, a method according to the invention includes the following steps: attaching at least one node to each bone segment to be moved; mapping the coordinates of each of the nodes in three-dimensional space; comparing the mapped coordinates with a desired configuration of the bone segments; and attaching rod mechanisms between pairs of nodes. Node pairs disposed on the same bone segment are designated as peer nodes and node pairs disposed on different bone segments are designated as remote nodes. The rod mechanisms utilized to connect pairs of nodes is at least one of extendible, retractable, and static along an axis thereof. At least one node from each bone segment is attached to a remote node by a rod mechanism that is pivotable with respect to both of the attached nodes in at least a first plane parallel to a plane tangent to the skull and in a second plane perpendicular to the first plane. The method further includes the step of extending at least one rod mechanism attached to one remote pair of nodes to achieve the desired configuration.

Other objects and advantages of the invention will be apparent to those skilled in the art from the following detailed description taken in conjunction with the drawings and the appended claims.

DETAILED DESCRIPTION OF THE INVENTION

Figures 1, 2:
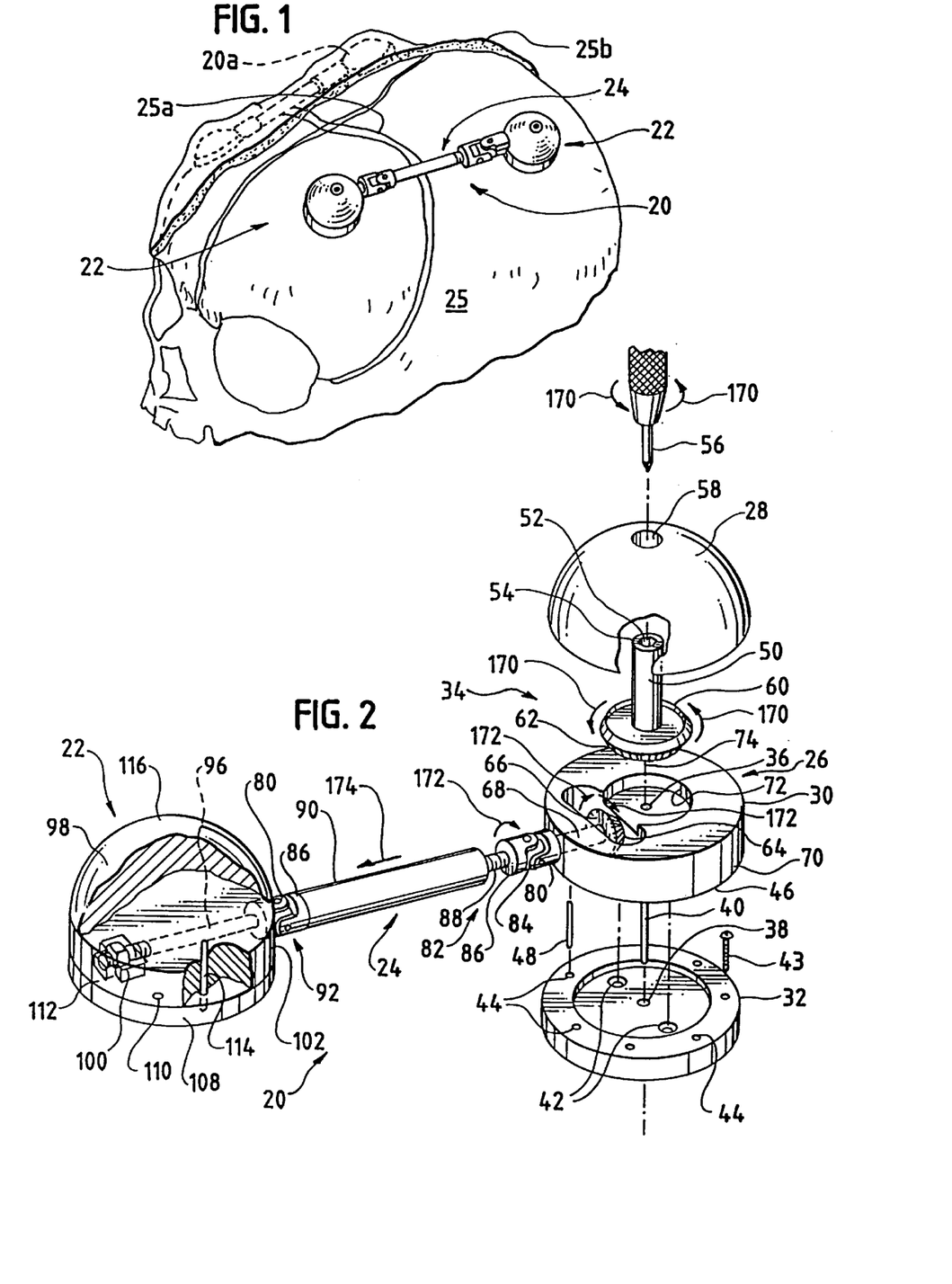
FIG. 1 is a perspective view of an apparatus according to the invention shown on a skull and showing a second apparatus according to the invention covered by a layer of skin.
FIG. 2 is an enlarged and partially expanded perspective view of the apparatus of FIG. 1, with certain portions cut away to show the detail thereof.

FIGS. 1 and 2 illustrate an apparatus according to the invention which is a basis of a craniotatic matrix according to the invention. The apparatus is a multi-axial node and rod unit, generally 20, which includes first and second nodes, generally 22 and a connected rod mechanism, generally 24. FIG. 1 shows an apparatus 20 according to the invention on an infant skull 25 with the rod mechanism 24 extending across the coronal suture 25a of the skull 25. FIG. 1 also shows a second apparatus 20a according to the invention shown in phantom disposed as it would be utilized on the skull 25 underneath a layer of skin 25b. The apparatus 20 and 20a are shown larger than the size of an apparatus of the invention which would be utilized on the infant skull 25 in order to provide a more detailed view of the apparatus.

Figures 7, 8:
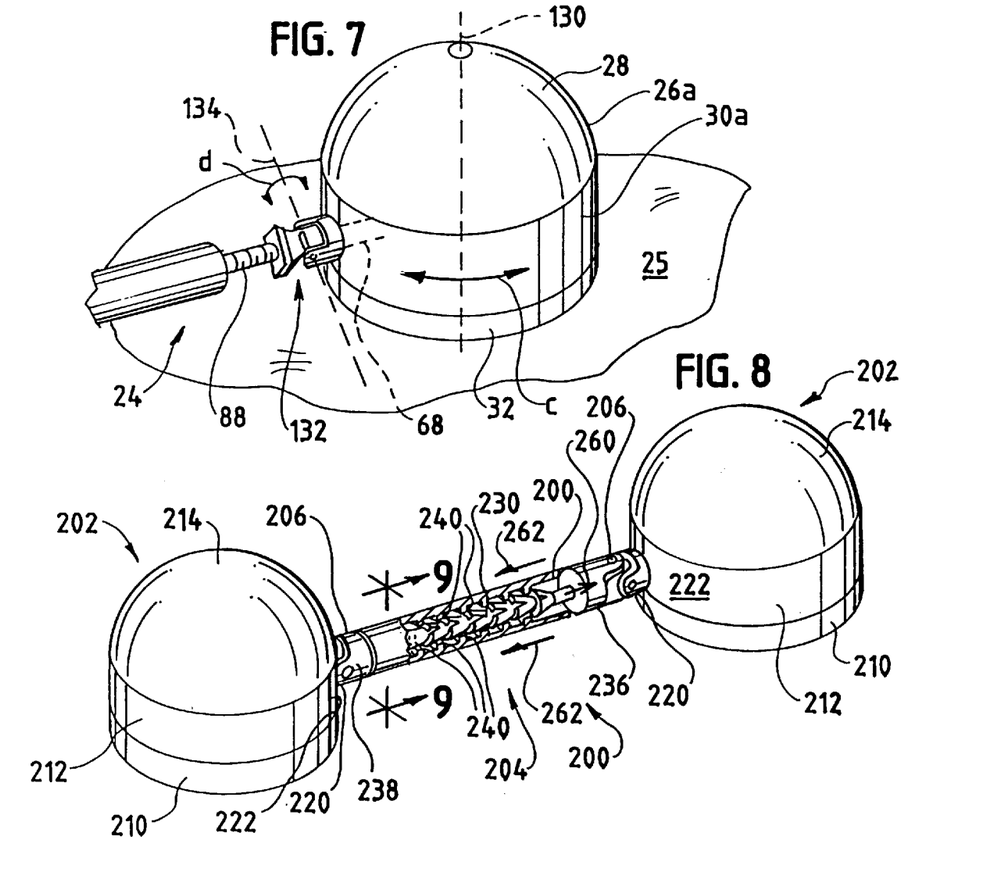
FIG. 7 is an enlarged partial view of a fourth embodiment of an apparatus according to the invention.
FIG. 8 is an enlarged perspective view of a fifth embodiment of an apparatus according to the invention with portions cut away to show the detail thereof.

FIG. 2 illustrates an embodiment of an apparatus according to the invention showing both the nodes 22 and the rod mechanism 24 in detail. The nodes and rod mechanism may be constructed of either stainless steel, silicone (or other plastic), or titanium, or a mixture of such materials. One of the nodes 22, identified generally by the reference numeral 26 in FIG. 2 includes a dome housing 28, a rod attachment portion 30 (which may be rotatable as shown in FIG. 7), and a non-rotating base for attachment to the skull 25 shown as a disk 32. A gear mechanism, generally 34, is disposed within a portion of the dome housing 28 and the rod attachment portion 30. The gear mechanism 34 is for rotating a portion of the rod mechanism 24.

The rod attachment portion 30 and the base 32 each have an aperture 36 and 38, respectively, through which a central shaft 40 extends. The central shaft 40 connects the non-rotatable base 32 with the rod attachment portion 30. The base 32 includes screw holes 42 through which bone screws 43 are inserted to attach the base 32 to the skull 25.

Figures 3, 4, 5:
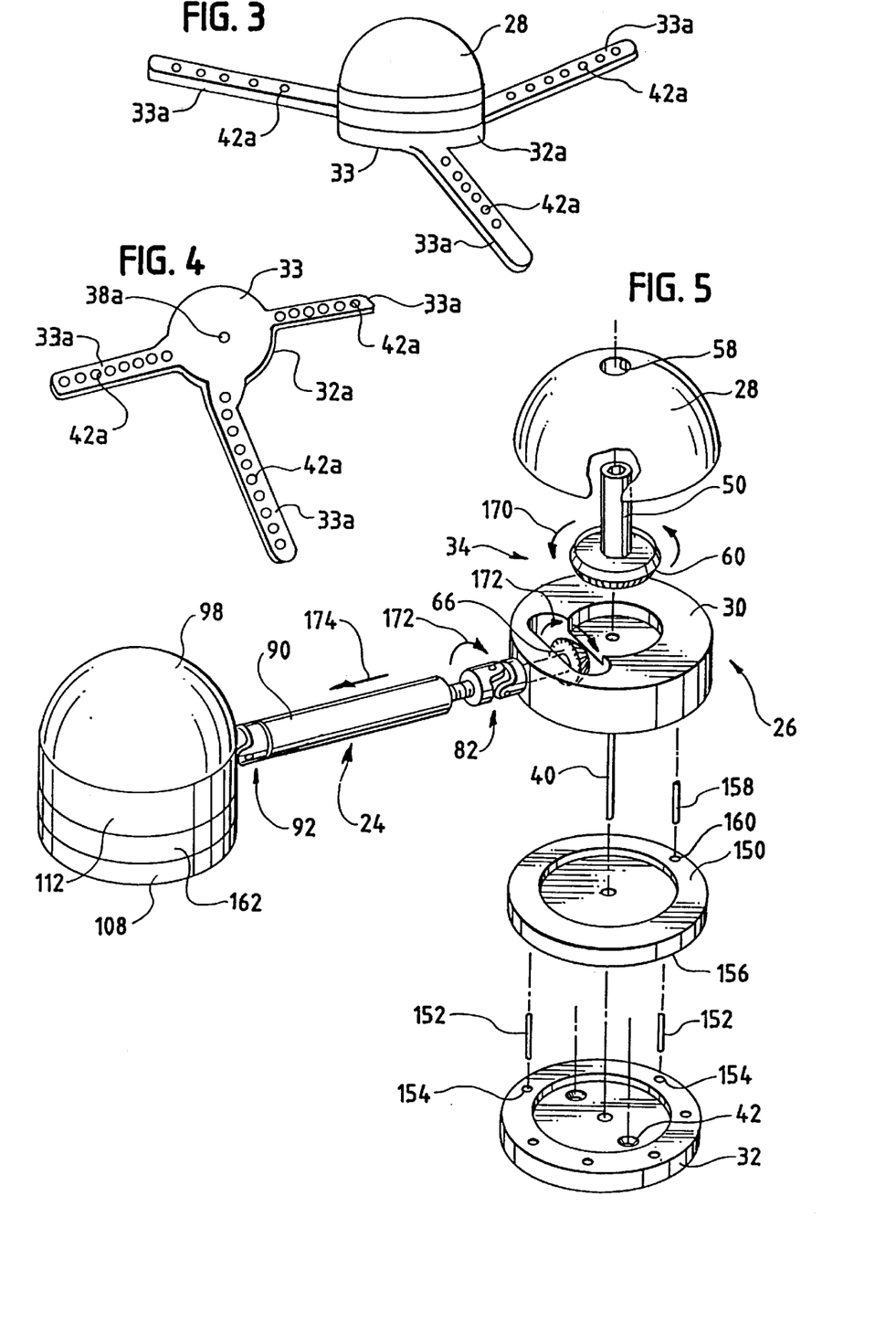
FIG. 3 is an enlarged perspective view of a second embodiment of an apparatus according to the invention.
FIG. 4 is a view taken along a back side of the embodiment shown in FIG. 3.
FIG. 5 is an enlarged and partially expanded perspective view of a third embodiment of an apparatus according to the invention.

FIGS. 3 and 4 illustrate an alternative embodiment according to the invention having a base 32a with a bottom surface portion 33 from which attachment arms 33a generally radially extend. The base 32a includes a central aperture 38a through which the central shaft 40 extends. The attachment arms 33a each have a plurality of screw holes 42a through which screws (now shown) are inserted to attach the base 32a to the skull 25.

Although FIGS. 3 and 4 show an embodiment of a base having three attachment arms 33a, depending upon the chosen location of the node, one, two, or more than three arms 33a may be preferred. The attachment arms 33a are preferably thin so as to be flexible and thus conform to the curvature of the skull when attached thereto. A base with one or more arms may be desirable when, for example, the armless base 32 shown in FIG. 2 would not provide adequate anchorage, such as at sites where the bone is weak or thin. Because such weak or thin anchorage sites might nonetheless be favorable for the placement of a node because of matrix geometry (as will be further discussed herein), a base with at least one arm as shown in FIGS. 3 and 4 provides an alternative to an armless base.

Figure 6:
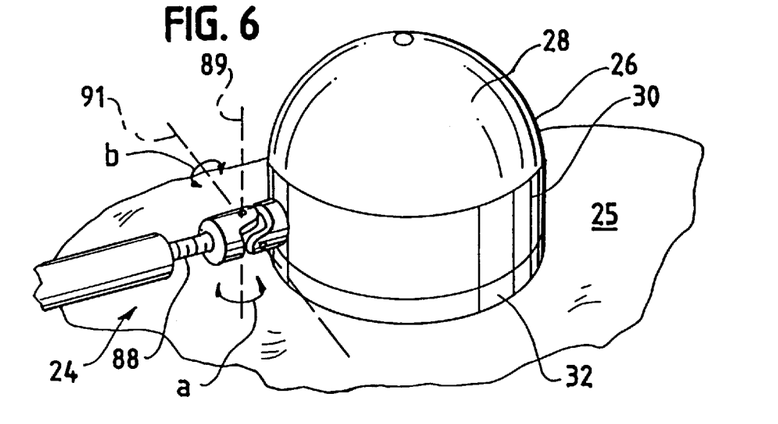
FIG. 6 is an enlarged partial view of the apparatus of FIGS. 1 and 2.

Returning to FIG. 2 and also to FIG. 6, the base 32 (and optionally the base 32a) includes a further aperture or apertures 44 which are aligned with corresponding apertures (not shown) extending into the rod attachment portion 30 at a surface 46 thereof. A pin 48 is inserted in the aperture 44 and the corresponding aperture in the rod attachment portion 30 to attach the base 32 to the rod attachment portion 30 in a non-rotating manner. Further pins 48 may be inserted in the additional apertures 44 in the base 32 and corresponding apertures in the rod attachment portion 30.

The gear mechanism 34 which is disposed in the rod attachment portion 30 and the dome housing 28 is a bevel gear system wherein two bevel wheels intermesh at an angle to change the direction of rotation of a shaft 50 disposed in the dome housing 28. The shaft 50 has a socket 52 at an end 54 thereof for activation by contact with an Allen wrench-type needle 56 which may be inserted through the skin 20a and an aperture 58 in the dome housing 28. A first gear wheel 60 of the mechanism 34 is fixed to the shaft 50 and includes gear teeth 62 which mesh with gear teeth 64 of a second gear wheel 66 attached to a shaft 68. The shaft 68 is perpendicular to the shaft 50 and extends through a housing 70 of the rod attachment portion 30 of the node 26. The first bevel gear wheel 60 is supported by a cradle 72 formed in the rod attachment portion 30. A base surface 74 of the wheel 60 includes an aperture into which the central shaft 40 extends.

The shaft 68 is attached to a first U-shaped arm 80 of a universal joint, generally 82. The universal joint 82 further includes a connector 84 and a second U-shaped arm 86, both arms being attached to the connector 84. The connector 84 may be in any suitable form, such as a ball or a cylinder. The second arm 86 is fixed to a threaded rod 88 of the rod mechanism 24. The shaft 68 is loosely mounted in the housing 70 to provide for rotation of the shaft 68 with respect to the housing 70. Thus, the rotation of the shaft 68, driven through the universal joint 82 results in the rotation of the threaded rod 88 about a longitudinal axis thereof.

Although a universal joint 82 is shown in the drawings of the application, other types of flexible joints may be utilized. For example, a flexible plastic coupling may be utilized to attach the shaft 68 to the rod 88. At minimum, the rod 88 of an extendable and/or retractable (referred to herein as "dynamic") node and rod unit according to the invention must be pivotable with respect to the node 26 in at least two dimensions which may be described as follows: The rod is pivotable with respect to the node in at least a first plane parallel to a plane tangent to the skull and also in a second plane perpendicular to the first plane. In other words, with respect to the embodiment of an apparatus according to the invention shown in FIGS. 2 and 6, the rod 88 is at least pivotable about a pivot axis 89 (pivot movement shown by the double arrow a) which provides for movement in a first plane parallel to a tangent plane (generally along the surface of the skull), and also pivotable about a pivot axis 91 (pivot movement shown by the double arrow b) which provides for movement in a second plane perpendicular to the first plane (generally toward and away from the surface of the skull).

With reference to FIG. 2, the threaded rod 88 extends into an elongate sleeve 90 having internal threads (not shown), the rod and sleeve forming a jack screw. The sleeve 90, which is co-axial with the rod 88, is attached to a second universal joint, generally, 92. The universal joint 92 is identical to the universal joint 82 and thus the same reference numerals are utilized to describe the parts thereof in FIG. 2. Specifically, the sleeve 90 is fixed to a U-shaped arm 86 attached to a connector 84, which is in turn attached to a U-shaped arm 80. The U-shaped arm 80 of the joint 92 is fixed to a threaded shaft 96 which extends through a body of a second node 98 and is fixed thereto by a bolt 100. It is noted that the U-shaped arm 80 of the joint 92 may be directly fixed to a surface 102 of the node 98. The arm 80 must be fixed in some manner to the node 98 because the sleeve 90 of the rod mechanism 24 must not rotate about a longitudinal axis thereof.

The node 98 also includes a base 108 having screw holes 110 through which screws (not shown) are inserted to attach the base 108 to a skull 25. The base 108 also may be equipped with one or more of the attachment arms 33a shown in FIGS. 3 and 4.

A rod attachment portion 112 and the base 108 each have an apertures through which a connector pin or pins 114 extend to attach the rod attachment portion 112 to the base 108. The connector pins 114 also extend into a dome housing 116 of the second node 98 for attachment of the dome housing 116 to the rod attachment portion 112. If the arm 80 of the second universal joint 92 is attached directly to the surface 102 of the node 98, the rod attachment portion 112 and dome housing 116 may be made from one piece.

As with the universal joint 82 and rod 88 coupling described herein, the universal joint 92 provides a flexible joint between the sleeve 90 and the node 98. At minimum, the sleeve 90 of a dynamic node and rod unit according to the invention must be pivotable with respect to the node 98 in at least two dimensions which may be defined by a first plane parallel to a plane tangent to the skull and also in a second plane perpendicular to the first plane.

FIG. 7 illustrates an alternative embodiment according to the invention having a node 26a which is identical to the node 26 described with respect to FIG. 2 with the exception that it has a rod attachment portion 30a which is rotatable about an axis 130. With reference to FIG. 2, the embodiment according to FIG. 7 does not include the pin 48 attaching the base 32 to the rod attachment portion 30. Thus, the action of the rod attachment portion 30a rotating about an axis 130 allows the rod 88 to pivot about the axis 130 (shown by the double arrow c) in a first plane parallel to a plane tangent to the skull.

In the embodiment shown in FIG. 7, the universal joint 82 is replaced by a hinge mechanism, generally 132, which connects the gear shaft 68 to the rod 88. The rod 88 is thus pivotable about a pivot axis 134 (pivot movement shown by the double arrow d) which provides for movement of the rod mechanism 24 in a second plane perpendicular to the first plane (generally toward and away from the surface of the skull). In the embodiments of apparatus according to the invention shown in FIGS. 2, 6, and 7, which include two universal joints 82 and 92, additional pivot planes are possible.

Another embodiment of an apparatus according to the invention shown in FIG. 5 is almost identical to the apparatus shown in FIG. 2. Thus, the same references numerals are utilized to show components identical to those shown in FIG. 2. The apparatus of FIG. 5 differs from the apparatus of FIG. 2 in that both of the nodes 22 include a shim portion or disk to provide additional distance between the rod mechanism 24 and the skull 25, where necessary, depending upon the curvature of the skull 25 at the location where the rod and node unit is mounted. With respect to the node 26 shown in FIG. 5, a shim 150 is disposed between the base 32 and the rod attachment portion 30. The shim 150 is non-rotatably attached to the base 32 by pins 152 which are inserted in apertures 154 of the base 32 and apertures (not shown) extending into the shim 150 at a surface 156 thereof. The shim 150 includes a central aperture through which the central shaft 40 extends. Also a pin 158 may be inserted into an aperture 160 of the shim 150 and a corresponding aperture (not shown) in the rod attachment portion 30 so that the rod attachment portion 30 does not rotate about the shaft 40. If rotation of the rod attachment portion 30 is desired, similar to the embodiment shown in FIG. 7, the pin 158 is omitted.

The embodiment shown in FIG. 5 also includes a shim 162 fixed between the base 108 and the rod attachment portion 112 of the node 98.

The embodiments shown in FIGS. 1–7, each show a dynamic node and rod unit, also called a coaxial pair, which may be implanted and utilized as follows: First, the unit is attached to a skull by fixing the base 32 to a first bone segment and the base 108 to a neighboring bone segment. As already noted herein a base 32a having one or more arms may attached to the skull in lieu of the base 32 or the base 108. To enable rapid positioning of the node during an operative procedure, the bases 32, 32a, or 108 may be applied to the bone of the skull 25 with special wide groove bone screws (not shown). Next, with respect to the node 26, the shim disk 150, if required, is placed on the base 32 in order to position the node high enough so the attached rod mechanism 24 clears the horizon of the skull 25. The node 98, if necessary, with the shim 162, are mounted in a similar manner. The remaining portions of the nodes 26 and 98 and the rod mechanism 24 are then attached.

The percutaneous port 58 disposed at the dome housing 28 permits entry of the needle wrench 56 into the dome housing 28 and the socket 52. The action of turning the wrench 56 in a direction indicated by the arrows 170 in the socket 52 rotates the first bevel gear wheel 60 in the same direction (as shown by the arrow 170), which in turn rotates the gear wheel 66 in a direction indicated by the arrows 172. The rod 88 is thus rotated in the same direction (as shown by arrows 172) about a longitudinal axis thereof (which also is the longitudinal axis of the sleeve 90), extending the threaded sleeve 90 in a direction indicated by the arrow 174. Thus, according to the invention, the needle-wrench 56 engages the gear mechanism 34 inside the node 26 which then drives the rod 88 through the flexible joint 82, extending the rod mechanism 24 by forcing the sleeve 90 away from the node 26 via the cooperation of the inner threads of the sleeve 90 and the outer threads of the rod 88.

Accordingly, if the needle-wrench 56 is turned in a direction opposite the arrows 170, the rod is turned in a direction opposite the arrows 172, rotating the threaded rod 88 within the threaded sleeve 90 such that the sleeve 90 is drawn toward the node 26 and thus retracting (i.e., shortening) the rod mechanism 24.

Figure 9:
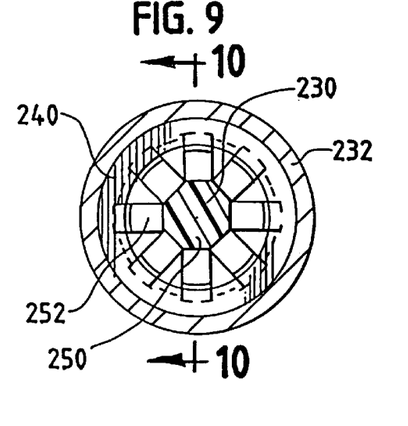
FIG. 9 is a cross-sectional view taken along line 9—9 of FIG. 8.
Figure 10:
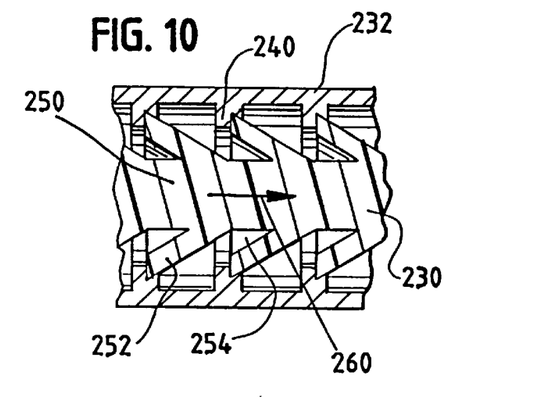
FIG. 10 is a longitudinal-sectional view taken along line 10—10 of FIG. 9.

In another embodiment of an apparatus according to the invention shown in FIGS. 8–10, an apparatus, generally 200, includes a rod mechanism which is a one-way rod ratchet system, generally 204, which incrementally advances a ratchet-toothed rod out of a sheath. Specifically, the apparatus 200 includes first and second nodes 202 connected to the rod mechanism 204 by first and second universal joints 206.

Each of the nodes 202 includes a base 210 which may be identical to the base 32 or the base 108 shown in FIG. 2 (or the base 32a of FIGS. 3 and 4). Each base 210 includes apertures (not shown) through which screws (not shown) extend to attach the base 210 to the skull 25. A rod attachment portion 212 is fixed to each base 210 and a dome 214 is attached to each rod attachment portion 212. The base 212, rod attachment portion 212, and dome 214 may be identical to the base 108, rod attachment portion 112, and dome 116 shown in FIG. 2 for the node 98 shown therein. A U-shaped arm 220 of each of the universal joints 206 which is contiguous to the rod attachment portion 212 may be directly fixed to a surface 222 of each of the nodes 202 or attached as shown with respect to the node 98 of FIG. 2. The arms 220 are preferably fixed with respect to the nodes 202.

The rod mechanism 204 includes a ratchet rod 230 disposed in an outer sleeve or sheathing rod 232. The ratchet rod 230 and the sheathing rod 232 are co-axial. The ratchet rod 230 is fixed to a U-shaped arm 236 of one of the universal joints 206 and the sheathing rod 232 is fixed to a U-shaped arm 238 of the other universal joint 206. The sheathing rod 232 has an annular cross-section and includes projections 240 spaced along a length of the rod 232, each projection 240 extending radially toward the longitudinal axis shared by the ratchet rod 230 and the sheathing rod 232. The projections 240 also have an annular cross-section.

The ratchet rod 230 includes a stem 250 and one-way teeth 252 extending therefrom. The teeth 252 are made from flexible material and each form an acute angle with the stem 250 as illustrated in FIG. 10 with a small triangular space 254 defined in part by a surface of the teeth and the stem 250. The ratchet rod stem 250 is disposed within a tubular space defined by the projections 240 of the sheathing rod 232. However each tooth 252 extends into a space defined by two projections 240 of the sheathing rod 232.

In order to extend the rod mechanism 204 shown in FIGS. 8–10, the ratchet rod 230 is powered out of the sheathing rod 232 in a direction 260 by bi-manual distraction provided by the clinician's hands (through the overlying skin) pulling the nodes 202 away from one another. The pulling force presses the projections 240 against the teeth 252, moving the teeth 242 toward the stem 250 and into the space 254, sliding the stem 250 and teeth 252 to a next (i.e., neighboring) space between projections 250, the teeth 252 springing back into an original orientation thereof upon reaching such space, providing for incremental movement of the sheathing rod 232 in a direction indicated by the arrows 262.

In another embodiment (not shown), the ratchet rod 230 is disposed with the teeth 252 extending in a direction opposite to that shown in FIGS. 8 and 10, to provide for a rod mechanism which can be retracted (i.e., shortened) by bi-manual contraction provided by the clinician's hands (through the overlying skin) pressing the nodes 202 toward one another.

The ratchet rod shown in FIGS. 8-10 may also be elongated (or retracted) by an embodiment (not shown) wherein a soft plastic dome 214 of the node 202 is depressed transcutaneously by the clinician's finger, powering a cam system (not shown) which advances the ratchet out of the sheath.

In a matrix or system according to the invention, rod and node units can be linked with other nodes and rods into a larger assembly which is capable of moving multiple bone segments in various directions. For example, please see FIGS. 12 and 13 which show a multi-axial craniotatic matrix encompassing an entire skull and FIGS. 14 and 15, each of which shows a multi-axial craniotatic matrix encompassing only a region of a skull.

Figure 11:
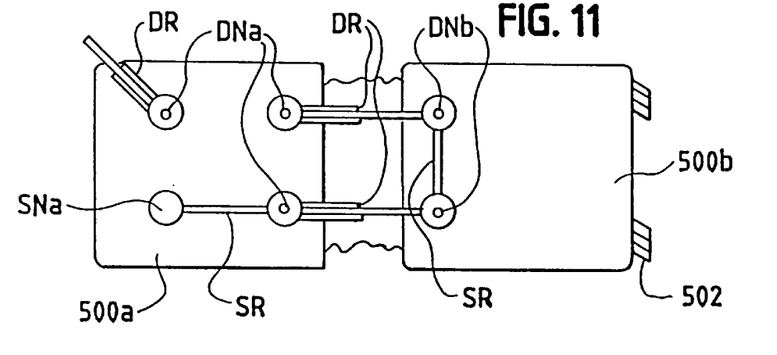
FIG. 11 is a schematic view of a craniotatic matrix according to the invention.
Figure 12:
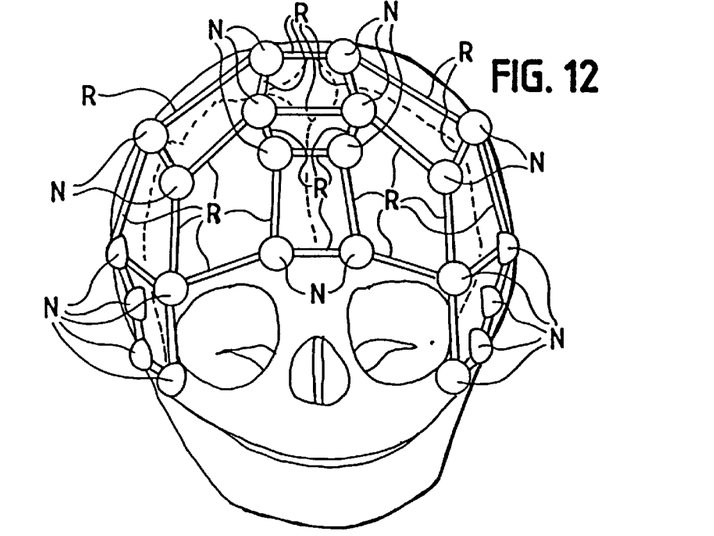
FIG. 12 is a partially schematic front view of a skull shown with a second embodiment of a craniotatic matrix according to the invention which encompasses the entire skull.
Figure 13:
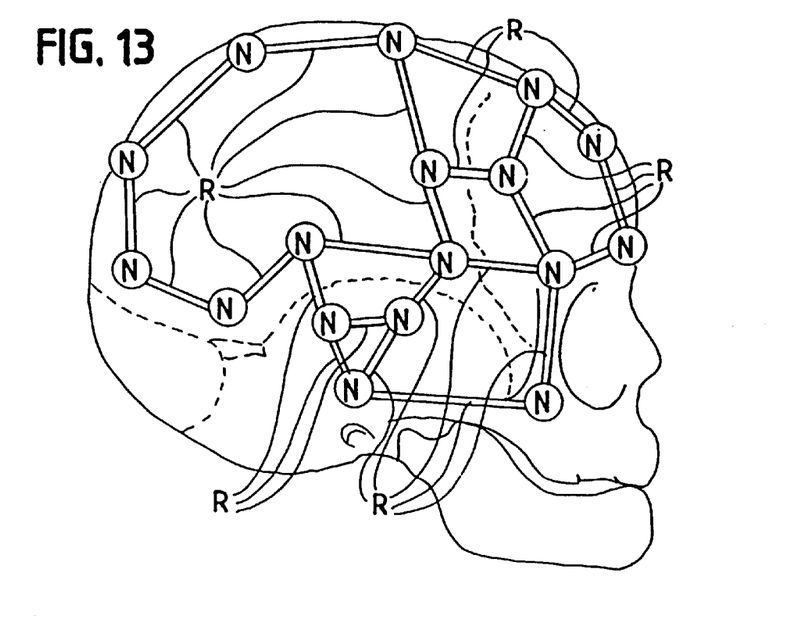
FIG. 13 is a partially schematic side view of the skull and matrix embodiment shown in FIG. 12.

With respect to FIGS. 12 and 13, the letter N designates a node which may be any of the types of nodes described herein with respect to FIGS. 1–10. The letter R designates rod mechanisms which also may be any of the types described herein with respect to FIGS. 1–10 and may also be a static rod (no extension or retraction mechanism). Each of the nodes N are anchorage units for the system and also serve as a landmark point for a guidance and tracking system according to the invention. The rod mechanisms R connect to the nodes N with varying degrees of rotational freedom (1 to 3 degrees of freedom). This means the rod mechanisms R may twist and rotate about their nodal connection N as required in order to provide the proper repositioning of the bone segments. An important action of a rod mechanism R is elongation between two nodes N anchored on separated bone segments so that the respective bone segments are distracted apart. It is also possible for the rod R to be shortened, thereby drawing two bone segments together. With reference to FIG. 11, a rod mechanism which can be extended and/or retracted is termed a dynamic rod mechanism DR because of its capability to change length. The rod mechanism 24 shown in FIG. 2 and the rod mechanism 204 shown in FIG. 8 are both dynamic rod mechanisms. Other rod mechanisms, termed static rods SR, are also connected to nodes N with varying degrees of freedom at the joints, but are not capable of changing length. The purpose of static rods SR is to distribute the distraction forces evenly throughout a bone segment. If extensive movement of a bone segment is necessary, then static rods SR avoid excessive concentration of force upon the bone anchoring a single node. Static rods are not necessary for lighter forces.

In a method according to the invention, each bone segment which requires corrective movement receives at least one node. Synostotically fused bone segments may be partitioned into smaller segments using surgical osteotomies (cuts) which divide the bone, yet do not lift the bones from the underlying soft tissue. One skull region or the entire skull may be encompassed by the matrix. A node may be connected by one to four rods which extend to other nodes.

With reference to FIG. 11, each bone segment which receives a node is termed a domain 500. The domains shown in FIG. 11 are domains 500a and 500b. The nodes local to a domain are termed peers. For example, the nodes of domain 500a identified as DNa and SNa are peers. Peer nodes which are connected to other peers by means of static rods SR are described as communicating. For example, the two nodes designated as DNb in the domain 500b are communicating peer nodes. Nodes residing on a separate segment of bone are termed remote. Two remote nodes united to a dynamic rod DR are termed a co-axial pair. Thus, each of the nodes DNa and DNb connected by a rod mechanism DR between the domains 500a and 500b of FIG. 11 are remote and are also each a co-axial pair. Domains are either dynamically or statically linked by the rods extending from domain to domain.

Therefore, with respect to FIG. 11, there is shown two dynamic rods linking two domains 500a and 500b. The domain 500a includes one set of communicating peers, two non-communicating peers, three co-axial nodes DNa, one static node SN, and one static rod SR. The domain 500b includes two communicating peers, and two co-axial nodes. Furthermore, the domain 500b is grounded as generally shown by a ground 502.

Figure 14:
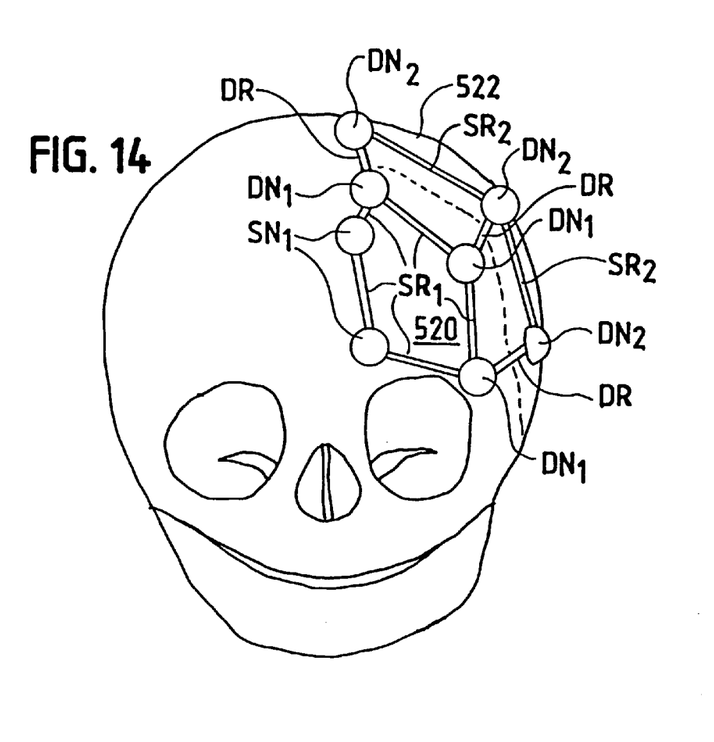
FIG. 14 is a partially schematic front view of a skull shown with a third embodiment of a craniotatic matrix according to the invention which encompasses a region of the skull.
Figures 15, 16:
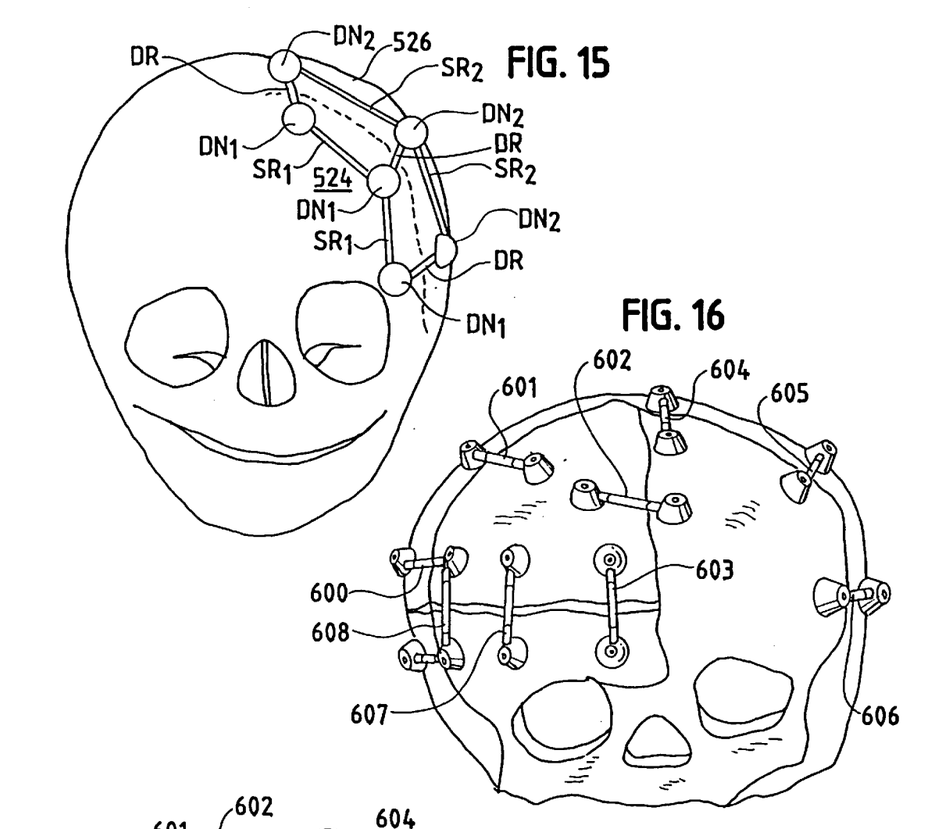
FIG. 15 is a partially schematic front view of a skull shown with a fourth embodiment of a craniotatic matrix according to the invention which encompasses a region of the skull.
FIG. 16 is a partially schematic front view of a skull shown with a fifth embodiment of a craniotatic matrix according to the invention which encompasses a region of the skull shown prior to the execution of distraction/compression steps according to a method of the invention.

The features of particular systems according to the invention are further illustrated in FIGS. 14 and 15. FIG. 14 illustrates dynamic peer nodes $DN_1$ and static peer nodes $SN_1$ occupying the same domain 520 connected by static rods $SR_1$ to form a closed circuit. FIG. 14 also illustrates three dynamic rods DR connecting co-axial pairs between dynamic nodes $DN_1$ and nodes $DN_2$ of a second domain 522.

FIG. 15 illustrates communicating dynamic peer nodes $DN_1$ occupying the same domain 524 connected by static rods $SR_1$ forming an open circuit. FIG. 13 also illustrates three dynamic rods DR connecting co-axial pairs between dynamic nodes $DN_1$ and nodes $DN_2$ of a second domain 526. Computer simulations have revealed improved stress reduction by the use of a closed circuit system shown in FIG. 14 as compared to an open circuit as shown in FIG. 15. Thus, the matrix shown in FIG. 14 may be desirable, for example, when resistance to bone distraction is great, the circuit of nodes spreading stress over a large area of the bone to be distracted.

Figure 17:
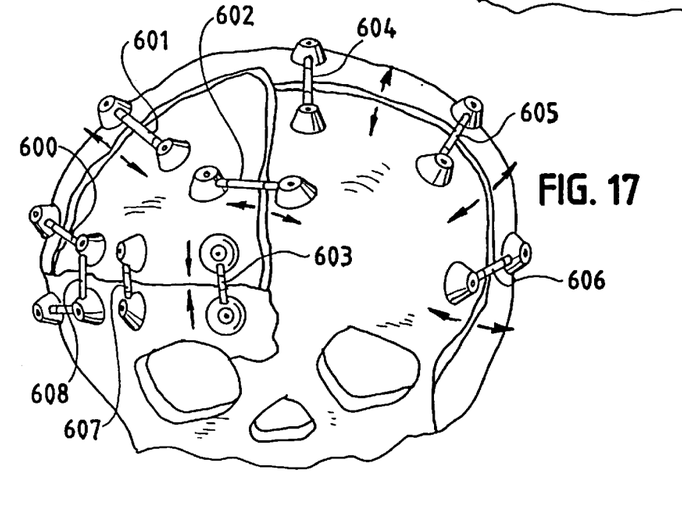
FIG. 17 is a partially schematic front view of a skull shown with the embodiment of a craniotatic matrix according to the invention shown in FIG. 16 shown subsequent to the execution of distraction/compression steps according to a method of the invention.

Further, with respect to FIGS. 16 and 17, a matrix according to the invention is shown before (FIG. 16), and after (FIG. 17) distraction and contraction steps according to a method of the invention. Each of the reference numerals 600 to 608 designate a co-axial pair (i.e., a dynamic rod and node unit according to the invention). In order to result in a skull configuration as shown in FIG. 17, the co-axial pairs 600, 601, 602, 604, 605, and 606 are extended while co-axial pairs 603, 607, and 608 are contracted.

According to the invention, the bone segments of the skull and face are either gradually separated, or drawn together according the therapeutic requirements of the craniofacial deformity. In order to follow (track) the morphology (shape) of the overall matrix the spacial location of the nodes are recorded with a 3-D coordinate measuring machine (CMM) currently available from several manufacturers (including Faro™) for medical-surgical adaptation and resale. A probe of the CMM is used to locate the nodes of the matrix. By locating the nodal coordinates in three dimensional space, the overall matrix can be mapped. Thus, by using the CMM, the overall morphology of the matrix is tracked and mapped utilizing a computer and appropriate software. Since the shape of the skull follows the shape of the matrix, the evolving healthy shape of the skull is thus guided. Guidance of matrix shape is achieved by modulating the rate of elongation (or contraction) of the component dynamic rods.

Since the matrix shape directly influences the shape of the skull, engineering physics is used to calculate on a computer the time-table of rod lengthenings, or shortenings necessary to achieve the desired shape. Computer based simplifications of the skull, termed primitives, form the basis of this calculation technique known as rigid body analysis. The primitives can also be displayed on the computer to demonstrate the major blocks of the skull in their stages of migration toward the desired conformation. A second computer based technique, termed finite element analysis (or method), can be used to map the stresses, strains, and deformations in the skull produced by the matrix.

The computer primitives may be compared to CT scans of the patients to present a more detailed view of the anatomy of the craniofacial skeleton as a desired terminal configuration is being reached.

EXAMPLE

I. Methods and Materials

Calibration trials were conducted on a dry adult calvarium to assess the reliability of 3D spline modeling and finite element methods specially reacted for the study. Computer programs were developed on a UNIX Sun Sparc 20 workstation to import, edge detect, and spline map the osseous contours of the craniofacial skeleton using axial CT images. The CT/FEM mesh was constructed and solved from the spline map wireframe using Structural Dynamics Research Corporation I-DEAS® Master Series Engineering Software. Comparison of strain gage data to strain values predicted from the finite element analysis showed agreement at $p \leq 0.05$ supporting extension of these procedures to routine clinical CT data (GE Medical Systems Advantage Series).

Distractive treatments were then simulated by CT/FEM on a 13-month old plagiocephalic infant with left unicoronal synostosis using various therapeutic rod and node matrix patterns and osteotomies. Physical and material properties were assigned to 4000 parabolic, color coded shell elements to compose an appliance-skull model including titanium, bone, dura, suture, synchondrosis, falx, tentorium, and osteotomy callus. Trials were conducted with both physiologic and elevated intracranial pressure applied to the endocranial surfaces. Active rod and node units (co-axial pairs), were applied between bone segments, described mechanically as domains, to construct various matrix patterns. The extent, or scope, of the patterns ranged from two to four domains consisting of one to six co-axial pairs. Patterns of increasing complexity were analyzed in the treatment of both cranial and orbital asymmetries.

II. Results

Mechanical distraction between any two domains altered the position of virtually every other domain in the infant craniofacial skeleton. Primary movement occurred on occupied domains and was consistently the most extensive. Motion diminished as secondary, and tertiary movement on successively remote domains. Greater therapeutic control was gained from judicious increase in the number of co-axial pairs and expansion of the matrix scope. By trial, anatomic correction appeared to be more dependent upon the overall pattern of the matrix than fastidious positioning of a specific co-axial pair. Greatest strain levels were reached within the osteotomy callus, greatest stress levels at the appliance anchorage sites, and mild yet detectable stress levels within the ipsilateral orbital apex. Furthermore, should the modulus of elasticity of the distracted osteotomy callus reach levels near $\frac{1}{100}$ that of the normal bone, the adjacent domains are placed at risk of sustaining noticeable bending deformation.

III. Conclusions

The direct mechanical consequences of cranial and upper facial distraction, including anatomic change, stress, and strain can be predicted by CT/FEM analysis. In addition to providing a rational basis for the application of distraction programs to geometrically complex deformities, such information is of import if mechanically based distractive treatment is to be correlated with final growth outcome.

The foregoing detailed description is given for clearness of understanding only, and no unnecessary limitations should be understood therefrom, as modifications within the scope of the invention will be apparent to those skilled in the art.

I claim:

1. An apparatus for correcting craniofacial bone deformities, said apparatus comprising:
   (a) a first node having a first base for fixation to a first segment of a skull;
   (b) a second node having a second base for fixation to a second segment of a skull;
   (c) a rod mechanism being at least one of extendible and retractable along an axis thereof;
   (d) a rod length adjustment mechanism disposed within the first node;
   (e) a first flexible joint attaching the first node and the rod length adjustment mechanism to the rod mechanism; and
   (f) a second flexible joint attaching the second node to the rod mechanism, the rod mechanism axis pivotable with respect to the first and second nodes in at least a first plane parallel to a plane tangent to the skull, the rod mechanism axis also pivotable with respect to the first and second nodes in a second plane perpendicular to the first plane.

2. The apparatus of claim 1 wherein the rod mechanism further comprises an outer sleeve having inner threads, the outer sleeve attached to the second flexible joint and fixed against rotation about the rod mechanism axis, and an inner rod extending into the outer sleeve and coaxial therewith, the inner rod having outer threads in communication with the inner threads of the outer sleeve, the inner rod attached to the first flexible joint; and
   the rod length adjustment mechanism comprising a gear mechanism disposed in the first node, the gear mechanism rotating the inner rod about the rod mechanism axis.

3. The apparatus of claim 2 wherein the gear mechanism further comprises:
   (a) a first shaft disposed in the first node, the first node having an aperture, the first shaft having an end, the end having a socket for engagement with a wrench-type needle;
   (b) a first bevel wheel having teeth and fixed to the first shaft;
   (c) a second bevel wheel having teeth meshing with the teeth of the first bevel wheel; and
   (d) a second shaft fixed to the second bevel wheel, the second shaft perpendicular to the first shaft, the second shaft connected to the inner rod by the first flexible joint.

4. The apparatus of claim 1 wherein the first and second bases each include at least one arm extending radially therefrom, the at least one arm having apertures for attachment to a bone by a bone screw.

5. The apparatus of claim 1 wherein the first node comprises:
   (a) a rod attachment portion adjacent the first flexible joint; and
   (b) a shim contacting the rod attachment portion, the shim being fixed to the first base.

6. The apparatus of claim 1 wherein the first node further comprises a rod attachment portion connected to the first base and adjacent to the first flexible joint, the rod attachment portion rotatable about an axis thereof, the first flexible joint being a hinge for pivoting the rod mechanism in the second plane.

7. The apparatus of claim 1 wherein the first node further comprises a rod attachment portion connected to the first base and adjacent to the first flexible joint, the rod attachment portion non-rotatable with respect to the first base, the first flexible joint being a universal joint.

8. The apparatus of claim 1 wherein the second flexible joint is a universal joint.

9. The apparatus of claim 1 wherein the rod mechanism further comprises:
   (a) an outer sleeve having spaced projections extending radially toward the rod mechanism axis, the outer sleeve being attached to the second flexible joint; and
   (b) an inner ratchet rod extending into the outer sleeve and coaxial therewith, the inner rod having a plurality of flexible teeth, each of said teeth partially disposable in a space defined by neighboring projections of the outer sleeve.

10. A matrix for correcting craniofacial bone deformities, said matrix comprising:
    (a) a first node configured to be disposed on a first bone segment;
    (b) a second node configured to be disposed on a second bone segment;
    (c) a first rod mechanism attached to both said first node and said second node by first and second flexible joints, respectively, the first rod mechanism being at least one of extendible and retractable along an axis thereof;
    (d) a third node configured to be disposed on one of the first bone segment, the second bone segment and a third bone segment neighboring the first bone segment; and
    (e) a second rod mechanism attached to said first node and said third node, the second rod mechanism being at least one of extendible, retractable, and static along an axis thereof.

11. The matrix of claim 10 wherein the first rod mechanism has an axis pivotable with respect to the first and second nodes in at least a first plane parallel to a plane tangent to the skull, the first rod mechanism axis also pivotable with respect to the first and second nodes in a second plane perpendicular to the first plane.

12. The matrix of claim 10 wherein the third node is configured to be disposed on the first bone segment and the second rod mechanism is static.

13. The matrix of claim 12 further comprising at least one additional node connected to both the first node and the third node by static rod mechanisms.

14. The matrix of claim 10 comprising at least a fourth node configured to be disposed on the first bone segment and an additional node configured to be disposed on the second bone segment, the fourth node and the additional node being attached by a third rod mechanism that is one of extendible, retractable and static.

15. A method of moving multiple bone segments in various directions, said method comprising the steps of:
    (a) attaching at least one node to each bone segment to be moved;
    (b) mapping the coordinates of each of the nodes in three-dimensional space;
    (c) comparing the mapped coordinates with a desired configuration of the bone segments;
    (d) attaching at least one rod mechanism to each node, attached node pairs disposed on the same bone segment being peer node pairs and attached nodes disposed on different bone segments being remote node pairs, the at least one rod mechanism being at least one of extendible, retractable, and static along an axis thereof, at least one node from each bone segment being attached to a remote node by one of said rod mechanisms to form a remote node pair, the rod mechanism being pivotable with respect to the remote node pair in at least a first plane parallel to a plane tangent to the skull and in a second plane perpendicular to the first plane; and (e) extending at least one rod mechanism attached to a remote pair of nodes to achieve the desired configuration.

16. The method of claim 15 including the step of retracting at least one other rod mechanism attached to a second pair of nodes to achieve the desired configuration.

17. The method of claim 15 further comprising the step of attaching at least one static rod between two peer nodes.

18. The method of claim 15 further comprising attaching a plurality of peer nodes onto a bone segment and attaching each peer node with a static rod to form a closed circuit of peer nodes to spread stress caused by the extending movement of step (e) across a portion of the bone segment upon which the plurality of peer nodes are disposed.

19. An apparatus for correcting bone deformities, said apparatus comprising:

(a) a first node adapted for subcutaneous fixation to a first segment of bone;

(b) a second node adapted for subcutaneous fixation to a second segment of bone;

(c) a rod mechanism adapted for subcutaneous placement between the first node and the second node, the rod mechanism being attached to the first node and the second node by at least one flexible joint and the rod mechanism being at least one of extendible and retractable along an axis thereof;

(d) a gear mechanism disposed in the first node, the gear mechanism coupled to the rod mechanism for at least one of extending and retracting the rod mechanism; and (e) a percutaneous access port formed in the first node, the percutaneous access port having an aperture, the aperture providing percutaneous access to the gear mechanism.

20. The apparatus of claim 19 wherein the rod mechanism further comprises (i) an outer sleeve having inner threads, the outer sleeve being attached to the second flexible joint and fixed against rotation about the rod mechanism axis and (ii) an inner rod extending into the outer sleeve and coaxial therewith, the inner rod having outer threads in communication with the inner threads of the outer sleeve, the inner rod being attached to the first flexible joint; and wherein the gear mechanism is coupled to the inner rod for rotating the inner rod about the rod mechanism axis.

21. The apparatus of claim 20 wherein the gear mechanism comprises:

(a) a first shaft disposed in the first node, the first shaft having an end, the end having a socket for engagement with a wrench-type needle, the socket being substantially aligned with the aperture;

(b) a first bevel wheel having teeth and being fixed to the first shaft;

(c) a second bevel wheel having teeth meshing with the teeth of the first bevel wheel; and (d) a second shaft fixed to the second bevel wheel, the second shaft being perpendicular to the first shaft and the second shaft connected to the inner rod.

22. The apparatus of claim 19 wherein the first node comprises a first base, the first base including at least one arm extending radially therefrom, said arm having apertures for attachment to a bone by a bone screw.

23. The apparatus of claim 19 wherein the first node comprises:

(a) a rod attachment portion; and (b) a shim contacting the rod attachment portion.

24. The apparatus of claim 19 wherein the rod mechanism further comprises;

(a) an outer sleeve having spaced projections extending radially toward the rod mechanism axis, the outer sleeve being attached to the second flexible joint; and (b) an inner ratchet rod extending into the outer sleeve coaxially therewith, the inner rod having a plurality of flexible teeth, each of said teeth being partially disposable in a space defined by neighboring projections of the outer sleeve.

25. An apparatus for correcting craniofacial bone deformities, said apparatus comprising:

(a) a first node having a first base adapted for fixation to a first segment of a skull;

(b) a second node having a second base adapted for fixation to a second segment of a skull;

(c) a rod mechanism being at least one of extendible and retractable along axis thereof, (d) a first flexible joint attaching the first node and the rod length adjustment mechanism to the rod mechanism;

(e) a second flexible joint attaching the second node to the rod mechanism, the rod mechanism axis being pivotable with respect to the first and second nodes in at least a first plane parallel to a plane tangent to the skull, the rod mechanism axis also being pivotable with respect to the first and second nodes in a second plane perpendicular to the first plane;

the rod mechanism comprising an outer sleeve having inner threads, the outer sleeve attached to the second flexible joint and fixed against rotation about the rod mechanism axis, and an inner rod extending into the outer sleeve coaxially therewith, the inner rod having outer threads in communication with the inner thread of the outer sleeve, the inner rod being attached to the first flexible joint; and a gear mechanism disposed in the first node, the gear mechanism rotating the inner rod about the rod mechanism axis.

26. The apparatus of claim 25 wherein the gear mechanism further comprises:

(a) a first shaft disposed in the first node, the first node having an aperture, the first shaft having an end, the end having a socket for engagement with a wrench;

(b) a first bevel wheel having teeth and being fixed to the first shaft;

(c) a second bevel wheel having teeth meshing with the teeth of the first bevel wheel; and (d) a second shaft fixed to the second bevel wheel, the second shaft being perpendicular to the first shaft, the second shaft being connected to the inner rod by the first flexible joint.

27. The apparatus of claim 26 wherein the first and second bases each include at least one arm extending radially therefrom, the at least one arm having apertures for attachment to a bone by a bone screw.

28. The apparatus of claim 25 wherein the first node comprises:

(a) a rod attachment portion adjacent the first flexible joint; and (b) a shim contacting the rod attachment portion, the shim being fixed to the first base.

29. The apparatus of claim 25 wherein the rod mechanism further comprises:

(a) an outer sleeve having spaced projections extending radially therefrom toward the rod mechanism axis, the outer sleeve being attached to the second flexible joint; and (b) an inner ratchet rod extending therefrom into the outer sleeve coaxially therewith, the inner ord having a plurality of flexible teeth, each of said teeth being partially disposable in a space defined by neighboring projections of the outer sleeve.

* * * * *